US009217852B2

United States Patent
Baleine (10) Patent No.: US 9,217,852 B2
(45) Date of Patent: Dec. 22, 2015

(54) SYSTEM AND METHOD FOR ONLINE INSPECTION OF TURBINES USING AN OPTICAL TUBE WITH BROADSPECTRUM MIRRORS

(75) Inventor: Erwan Baleine, Orlando, FL (US)

(73) Assignee: Siemens Energy, Inc., Orlando, FL (US)

(*) Notice: Subject to any disclaimer, the term of this patent is extended or adjusted under 35 U.S.C. 154(b) by 700 days.

(21) Appl. No.: 13/597,919

(22) Filed: Aug. 29, 2012

(65) Prior Publication Data
US 2014/0063227 A1   Mar. 6, 2014

Related U.S. Application Data

(63) Continuation-in-part of application No. 13/362,308, filed on Jan. 31, 2012, now Pat. No. 8,896,661, and a continuation-in-part of application No. 13/362,365, filed on Jan. 31, 2012.

(51) Int. Cl.
G01J 5/00      (2006.01)
G02B 17/06     (2006.01)
G01N 21/00     (2006.01)
G02B 23/24     (2006.01)
G01N 21/95     (2006.01)
G01N 21/954    (2006.01)

(52) U.S. Cl.
CPC ............ *G02B 17/0652* (2013.01); *G01N 21/00* (2013.01); *G01N 21/95* (2013.01); *G01N 21/954* (2013.01); *G02B 23/2492* (2013.01)

(58) Field of Classification Search
CPC .............................. G01N 21/00; G01N 21/954
USPC .................. 250/338.1, E7.085; 359/838, 850
See application file for complete search history.

(56) References Cited

U.S. PATENT DOCUMENTS

| 2,010,014 | A |   | 8/1935 | Elliott |
|-----------|---|---|--------|---------|
| 2,011,006 | A |   | 8/1935 | Maclean |
| 4,459,043 | A | * | 7/1984 | Luke ............................. 374/130 |
| 4,939,043 | A | * | 7/1990 | Biricik et al. ................. 428/620 |

(Continued)

FOREIGN PATENT DOCUMENTS

| EP | 2023180 | 2/2009 |
|----|---------|--------|
| GB | 2075212 | 11/1981 |

(Continued)

OTHER PUBLICATIONS

Hass, Georg, Journal of the Optical Soceity of America, vol. 39, No. 7, pp. 532-540, Jul. 1949.*

*Primary Examiner* — David Porta
*Assistant Examiner* — Meenakshi Sahu (57) ABSTRACT

An optical inspection system for nondestructive internal visual inspection and non-contact infra-red (IR) temperature monitoring of an online, operating power generation turbine. The optical inspection system includes an optical tube having a viewing port, at least one reflective mirror or a mirror array having a reflectivity spectral range from 550 nm to 20 μm, and capable of continuous operation at temperatures greater than 932 degrees Fahrenheit (500 degrees Celsius), and a transparent window with high transmission within the same spectral range mounted distal the viewing port. The same optical mirror array may be used to measure selectively surface temperature of metal turbine blades in the near IR range (approximately 1 μm wavelength) and of thermal barrier coated turbine blades in the long IR range (approximately 10 μm wavelength).

20 Claims, 5 Drawing Sheets

(56) References Cited

U.S. PATENT DOCUMENTS

| | | | |
|---|---|---|---|
| 5,097,110 A * | 3/1992 | Hamada et al. | 219/121.63 |
| 5,461,445 A | 10/1995 | Kikuchi | |
| 5,555,480 A | 9/1996 | Tanaka et al. | |
| 5,670,784 A | 9/1997 | Cusack et al. | |
| 5,723,078 A * | 3/1998 | Nagaraj et al. | 264/36.18 |
| 6,459,481 B1 | 10/2002 | Schaack | |
| 8,896,661 B2 * | 11/2014 | Baleine et al. | 348/36 |
| 2002/0136548 A1 | 9/2002 | Fuss | |
| 2005/0281520 A1 | 12/2005 | Kehoskie et al. | |
| 2008/0144186 A1 | 6/2008 | Feng et al. | |
| 2008/0297808 A1 | 12/2008 | Riza et al. | |
| 2009/0027665 A1 | 1/2009 | Ogburn et al. | |
| 2010/0140373 A1 | 6/2010 | Myhre et al. | |
| 2010/0168981 A1 | 7/2010 | Kominsky | |
| 2010/0220182 A1 | 9/2010 | Krull et al. | |
| 2010/0321703 A1 | 12/2010 | Harpin et al. | |
| 2011/0069165 A1 | 3/2011 | Zombo et al. | |
| 2011/0229307 A1 | 9/2011 | Lemieux et al. | |
| 2011/0261253 A1 | 10/2011 | Chang | |
| 2012/0019905 A1 | 1/2012 | Teraoka et al. | |
| 2013/0194411 A1 * | 8/2013 | Baleine et al. | 348/82 |

FOREIGN PATENT DOCUMENTS

| | | |
|---|---|---|
| GB | 2075212 A | 11/1981 |
| GB | 2087588 | 5/1982 |
| GB | 2087588 A | 5/1982 |
| JP | 03200109 | 9/1991 |
| JP | 2005227405 | 8/2005 |
| JP | 2006039319 | 2/2006 |
| JP | 2008242310 | 10/2008 |
| JP | 2010085715 | 4/2010 |
| JP | 2003-215470 | 12/2011 |

* cited by examiner

SYSTEM AND METHOD FOR ONLINE INSPECTION OF TURBINES USING AN OPTICAL TUBE WITH BROADSPECTRUM MIRRORS

CROSS-REFERENCE TO RELATED APPLICATIONS

This application is a continuation-in-part of both co-pending United States utility patent applications entitled "SYSTEM AND METHOD FOR ONLINE INSPECTION OF TURBINES INCLUDING ASPHERIC LENS", assigned Ser. No. 13/362,308, now U.S. Pat. No. 8,896,661, issued Nov. 25, 2014, and "SYSTEM AND METHOD FOR ONLINE INSPECTION OF TURBINES INCLUDING TEMPERATURE AND VIBRATION COMPENSATING LENS MOUNT", assigned Ser. No. 13/362,365, both of which were filed Jan. 31, 2012, and are incorporated by reference herein.

STATEMENT REGARDING FEDERALLY SPONSORED DEVELOPMENT

Development for this invention was supported in part by Contract No. DE-FC26-05NT42644, awarded by the United States Department of Energy. Accordingly, the United States Government may have certain rights in this invention.

BACKGROUND OF THE DISCLOSURE

1. Field of the Invention

The invention relates to an optical system for nondestructive internal inspection and temperature monitoring of online power generation turbines, including gas turbines with either metal or thermal barrier coated (TBC) turbine blades that are operating with surface temperatures in the range of over 600° C. (1112° F.). More particularly, the present invention relates to an optical system, including an optical tube utilizing a series of mirrors having a spectral reflectivity range from the visible to the long wave infrared, namely 550 nm to 20 μm for gold mirror, and capable of continuous operation at temperatures greater than 932 degrees Fahrenheit (500 degrees Celsius). The same reflective optical system may be used to measure selectively surface temperature of metal turbine blades in the near IR range (approximately 1-2 μm wavelength) and of thermal barrier coated turbine blades in the long IR range (approximately 8-12 μm wavelength).

2. Description of the Prior Art

Infra-red or visible spectrum online camera systems monitor critical internal engine components of a power generation gas turbine, steam turbine, generator or their associated equipment during their operation in a power plant, by combining a high temperature refractive lens optical system with high-speed camera imagery. The optical system design requires selection and combination of lenses and optical material in order to provide the best image quality compatible with the inspected component's emissivity, while surviving within the harsh operating environments of the equipment. It is also preferable, where possible, to use the same optical inspection system components across a broad spectrum of inspection wavelengths for multiple applications in multiple types of internal engine components.

For example, metal turbine blades have high emissivity in the near infra-red 1-2 μm wavelength range. There are suitable refractive lens materials that offer good transmissivity in the near and mid IR 1-5 μm wavelength range that can resist hostile temperature environments of approximately 1000° C. (~1830° F.) within operating gas turbine blade sections. Thus, camera monitoring systems coupled to those refractive lens optical systems in the near IR range generate good quality images that can be used, among other things, for accurate metal blade surface temperature measurement.

In contrast, gas turbine blades having thermal barrier coatings (TBC) have a high emissivity value in the long IR range around 8-12 μm wavelength. Thus, long IR imaging is preferred for measuring gas turbine TBC blade surface temperature. The 8-12 μm detection band can provide accurate TBC blade surface temperature measurement. However, it is challenging to find suitable long IR refractive lens optical materials that are as robust for optical tubes used in a gas turbine environment as the near IR refractive materials used in near IR optical system optical tubes.

Robust optical tubes are needed in the industry for the continuous online monitoring of internal turbine parts during their entire operating lifecycle. Gas turbines are intended to be operated continuously between scheduled maintenance cycles. The optomechanical components of camera inspection systems cannot be removed from a monitored gas turbine during the latter's operation, until a scheduled maintenance period. Typical maintenance inspection cycles of gas turbines are scheduled every 4000 hours, with typically a major inspection every 8000 hours. It is therefore critical for a continuous online inspection monitoring system to remain operational without disassembly at least 4000 hours before it has a chance to be inspected and serviced.

Thus, a need exists in the art for a high temperature environment inspection system for power system turbines and the like that can withstand continuous operation in temperature environments above 500° C. (932° F.) and desirably up to 1000° C. (1832° F.).

There is another existing need to increase optical transmission efficiency while maintaining and preferably increasing image quality across a multispectral imaging wavelength range without the need to use different optical tubes for different inspection applications.

There is another overall need in the art to increase high temperature inspection system operational service life so that it coincides with scheduled turbine maintenance service periods: desirably for 4000 hours.

SUMMARY OF THE INVENTION

Accordingly, an object of the invention is to create a high temperature environment inspection system for power system turbines and the like that can withstand continuous operation in temperature environments above 500° C. (932° F.) and desirably up to 1000° C. (1832° F.).

Another object of the invention is to increase optical transmission efficiency of optical tubes in optical inspection systems that provide high image quality across a multispectral imaging range, including the near IR range and the long IR range, without the need to use different optical tubes for different inspection applications.

There is another overall need in the art to increase high temperature inspection system operational service life so that it coincides with scheduled turbine maintenance service periods: desirably for 4000 hours.

These and other objects are achieved in accordance with the present invention by an optical inspection system for nondestructive internal visual inspection and non-contact infra-red (IR) temperature monitoring of an online, operating power generation turbine. The optical inspection system includes an optical tube having a viewing port, at least one mirror having a spectral reflectivity range from 550 nm to 20

μm, and capable of continuous operation at temperatures greater than 932 degrees Fahrenheit (500 degrees Celsius), and a transparent window with high transmission within the same spectral range mounted distal the viewing port. The optical tube may comprise a series of mirrors. The same optical system may be used to measure selectively surface temperature of metal turbine blades in the near IR range (approximately 1-2 μm wavelength) and of thermal barrier coated turbine blades in the long IR range (approximately 8-12 μm wavelength).

The invention features a turbine inspection apparatus having an optical tube housing having a viewing port; and at least one mirror mounted within the housing in optical alignment with the viewing port, the mirror having spectral reflectivity from 550 nm to 20 μm, and capable of continuous operation at temperatures greater than 932 degrees Fahrenheit (500 degrees Celsius).

Additionally, embodiments of the invention feature a turbine camera inspection system including an optical tube housing having a viewing port. At least one mirror is mounted within the housing in optical alignment with the viewing port. The mirror has a spectral reflectivity from 550 nm to 20 μm wavelengths, and is capable of continuous operation at temperatures greater than 932 degrees Fahrenheit (500 degrees Celsius). A transparent window is mounted within the housing distal the viewing port in optical alignment with the at least one mirror. The window has a spectral transmission band from 550 nm to 20 μm wavelength and is capable of continuous operation at temperatures greater than 572 degrees Fahrenheit (300 degrees Celsius). The reflector lens array transmits within the housing through the window an image of an object of interest that is oriented within a field of view established by the at least one mirror. The optical tube may comprise a series of mirrors. A camera is coupled to the housing in optical alignment with the window and the at least one mirror, for capturing images formed by the optical system.

The invention also features a method for visually inspecting in the infra-red (IR) spectrum areas of interest within an operating gas turbine with an IR camera inspection system having: an optical tube housing having a viewing port; at least one mirror mounted within the housing in optical alignment with the viewing port, the mirror having spectral reflectivity from 550 nm to 20 μm, and capable of continuous operation at temperatures greater than 932 degrees Fahrenheit (500 degrees Celsius); a transparent window mounted within the housing distal the viewing port in alignment with the at least one mirror having spectral transmissivity from 550 nm to 20 μm; the at least one mirror transmitting within the housing through the window an image of an object of interest that is oriented within a field of view established by the optical system; and a camera coupled to the housing in alignment with the system, for capturing the image formed by the optical system. The optical tube may comprise a series of mirrors. The inspection method is performed by inserting the camera inspection system housing viewing port into an inspection port of a gas turbine and generating images of areas of interest within the gas turbine during turbine operation.

The objects and features of the present invention may be applied jointly or severally in any combination or sub-combination by those skilled in the art.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

After considering the following description, those skilled in the art will clearly realize that the teachings of my invention can be readily utilized in an optical inspection system for nondestructive internal visual inspection and non-contact infra-red (IR) temperature monitoring of an online, operating power generation turbine. The optical inspection system includes an optical tube having a viewing port, at least one non-planar mirror having a reflectivity spectral range from 550 nm to 20 μm, and capable of continuous operation at temperatures greater than 932 degrees Fahrenheit (500 degrees Celsius), and a transparent window with high transmission within the same spectral range mounted distal the viewing port. The optical tube may comprise a series of mirrors. The same series of mirrors may be used to measure selectively surface temperature of metal turbine blades in the near IR range (approximately 1-2 μm wavelength) and of thermal barrier coated turbine blades in the long IR range (approximately 8-12 μm wavelength). Thus a single optical tube design can be utilized to inspect and obtain remote non-contact surface temperature readings of turbines incorporating either metal turbine blades or thermal barrier coated turbine blades.

Figure 1:
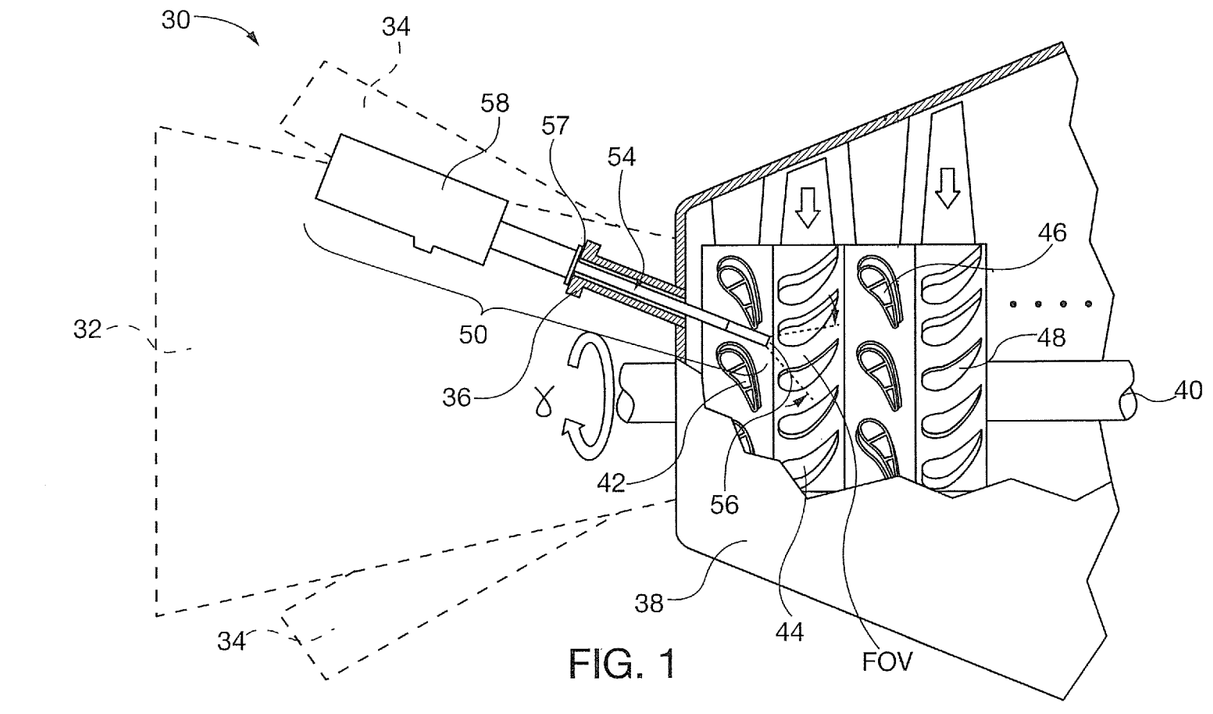
FIG. 1 is a schematic elevational view of a gas turbine being inspected with a camera inspection system of the present invention.

FIG. 1 shows schematically a known gas turbine 30 having a compressor section 32, a plurality of circumferential combustors 34 and a turbine section 38 through which passes rotating shaft 40. The turbine section 38 includes stationary row 1 vanes 42, as well as row 1 blades 44 that are rotatively coupled to the shaft 40. The turbine section 38 includes successive alternating rows of stationary vanes and rotating blades, such as row 2 vanes 46 and row 2 blades 48. The turbine 30 incorporates a plurality of inspection ports, including exemplary inspection port 36, to facilitate inspection access to internal components.

As shown in FIG. 1, an embodiment of a camera inspection system 50 is coupled to inspection port 36, and includes an optical tube housing 54 with a viewing port 56 that establishes a field of view (FOV) that is aligned with the housing central axis. Alternatively a field of view can be aligned at an angle skewed to the central axis by incorporating a mirror or prism to redirect the image through the housing central axis. Flange 57 on optical tube housing 54 is coupled to the inspection port 36. Camera enclosure 58 captures images transmitted by mirror array 60 and repeater mirror arrays 60', 60" in the optical tube housing 54. The camera inspection system 50 is useful for inspecting areas of interest within the turbine 30 visible in the field of view, such as for example monitoring surface temperature of the leading edges of row 1 turbine blades 44 by known non-contact infrared (IR) thermal imaging systems. While FIG. 1 shows use of a single inspection system 50, two or more inspection systems in different inspection ports can be used simultaneously or serially in any combination at the discretion of the system user.

Figure 2:
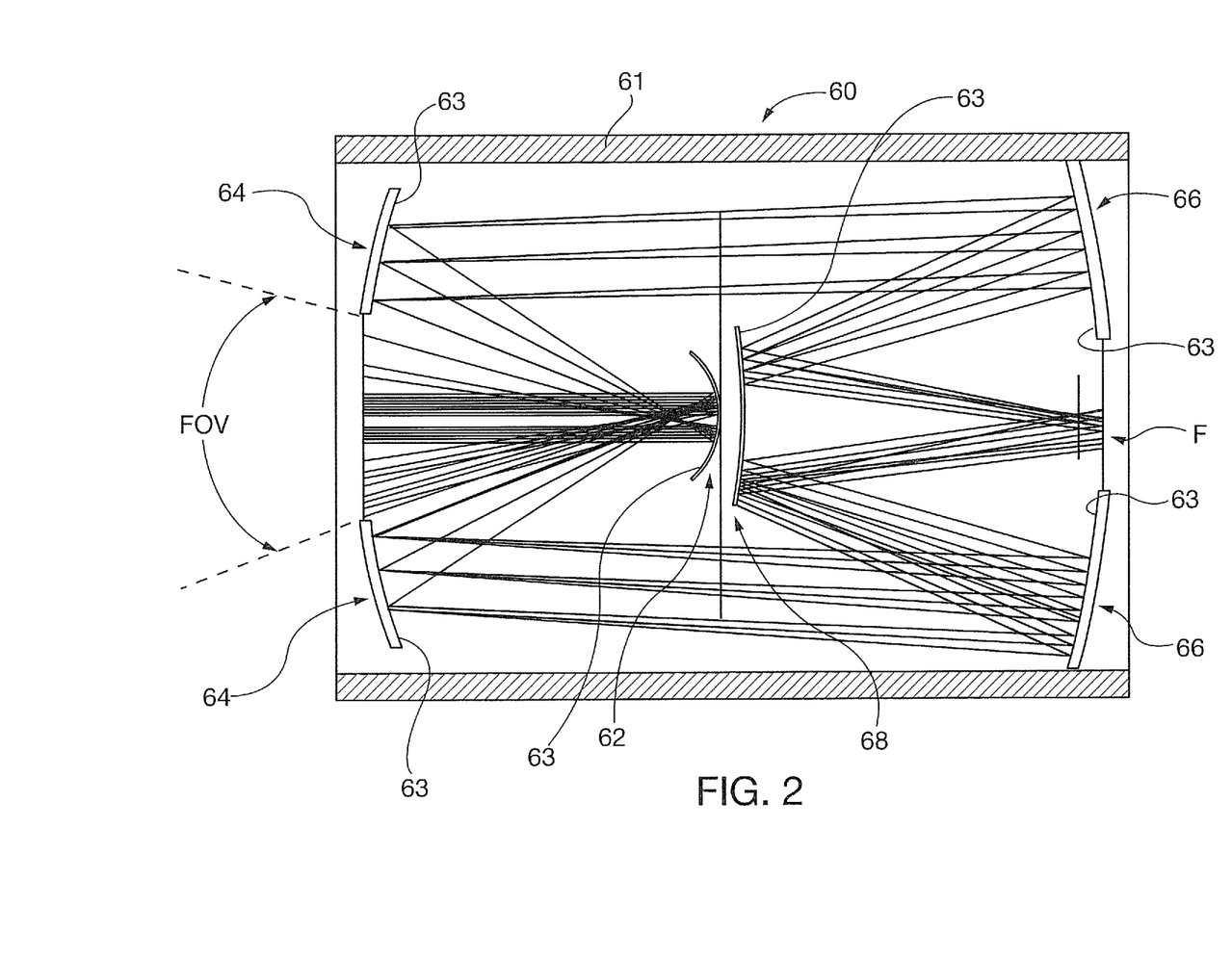
FIG. 2 is a schematic elevational view of an embodiment of a reflective optical system of the present invention, for forming an image of an object of interest located within a field of view (FOV)

FIG. 2 shows a schematic embodiment of an exemplary reflective mirror array 60 that is used in the optical inspection system of the present invention. The reflective mirror array 60 captures an image within its objective field of view (FOV) and transmits the image to an ocular focal plane F. The mirror array 60 is retained within a mirror housing 61, preferably comprising a temperature resistant metal capable of sustained operation at temperatures equal to or greater than 500° C. (932° F.). Concave mirror 62, optionally having a coating surface 63 reflects the FOV image to an objective reflector mirror 64 that in turn relays the image to an ocular reflector mirror 66. The image reflected by reflector mirror 66 is relayed to convex mirror 68 that focuses the image along focal plane F. The optical array assembly 60 dimensions are selected, using known optical principles, to be packaged within the optical tube housing 54 dimensions, set field of view angle and focal plane axial length, and image magnification (if any).

Optical array assembly 60 components preferably comprise heat resistant metals capable of sustained operation at temperatures equal to or greater than 500° C. (932° F.). Mirror elements 62, 64, 66, 68 comprise heat resistant glass or metal substrates with a reflective surface metal coating layer 63 applied by known methods, such as sputter coating. Suitable coating material layers comprise gold (Au) and molybdenum (Mb), preferably with a chromium (Cr) adhesion layer for enhancing high-temperature heat resistance. Gold has spectral reflectivity in a broad wavelength bandwidth from approximately 550 nm to 20 μm and does not introduce any chromatic aberration. The Gold reflectivity bandwidth covers the visible, near IR and far IR spectra, making it suitable for turbine blade metal surface or thermal barrier coated surface inspection, including non-contact temperature monitoring. Thus, an optical tube including the gold- or molybdenum-coated reflector mirror array assembly embodiments of the present invention, can be utilized for multiple inspection applications for both metal and thermal barrier coated turbine blades.

Figure 3:
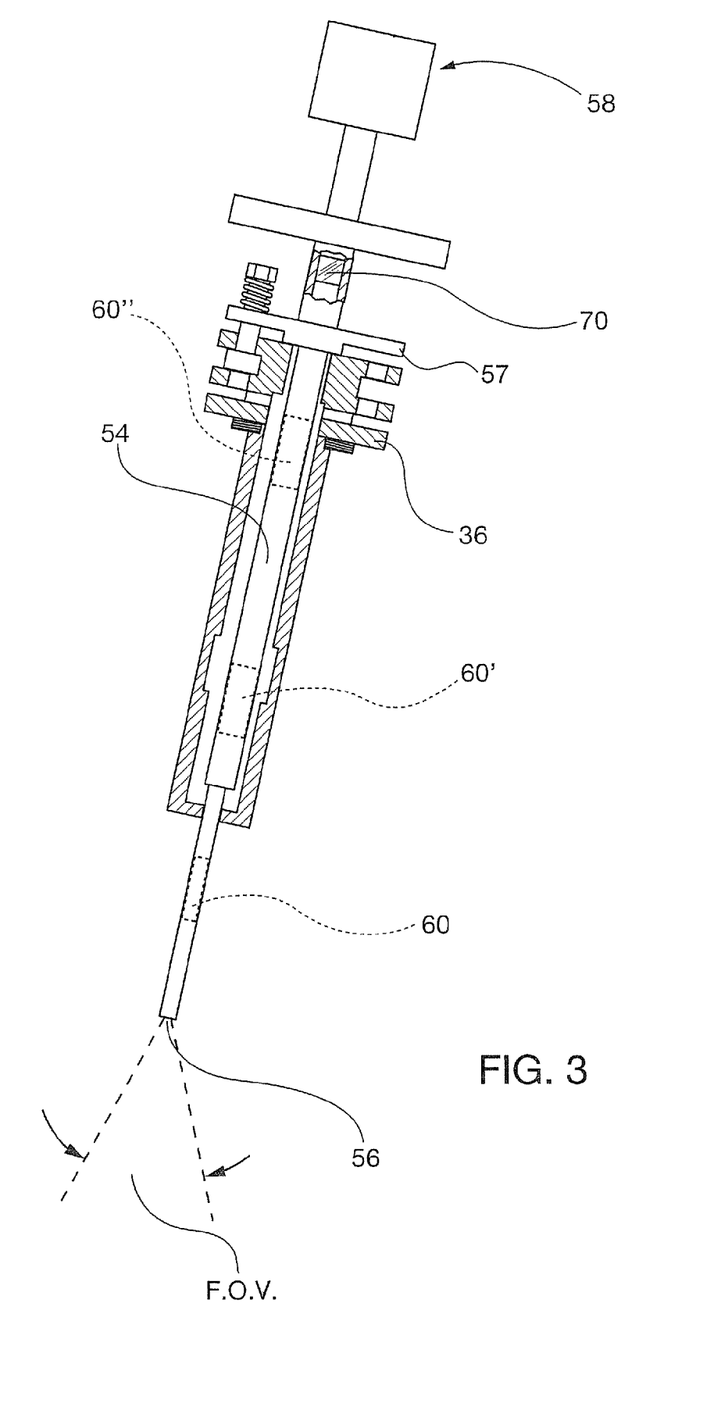
FIG. 3 is a partial axial cross-sectional view of an optical tube housing of an embodiment of the present invention incorporating a series of mirrors of FIG. 2, wherein an image is taken in line with the tube central axis.

Optical tube housing 54 internal construction is shown schematically in FIG. 3. The optical tube housing 54 is shown inserted within turbine inspection port 36, and is affixed in sealed fashion to the inspection port by known construction flange 57, so that turbine combustion gasses do not exit the inspection port. The optical tube embodiment shown in FIG. 3 has a series of three optically aligned reflective mirror arrays or assemblies 60, 60', 60" that capture an image field of view established by the viewing port 56 and relay it to the camera enclosure 58 that is external the turbine 30. The number and dimensions of relays 60, etc. is selected to capture the image field of view and relay it to the camera enclosure 58. The end of optical tube 54 distal from the viewing port 56 is sealed with transparent refractive pressure window 70, to prevent exhaust of turbine combustions gas. The window 70 is located external the turbine inspection port 36 and its operational temperature does not exceed 300° C. The external refractive pressure window 70 comprises material having complimentary transmission quality to the reflective lens array 60, etc., in the long IR wavelength range, that is capable of sustaining 300° C. continuous operational temperatures. The refractive pressure window 70 preferably comprises zinc selenide (ZnSe). Other refractive materials, having transmittance properties compatible with the optical system's desired inspection wavelength range, may be substituted for zinc selenide.

Figure 4:
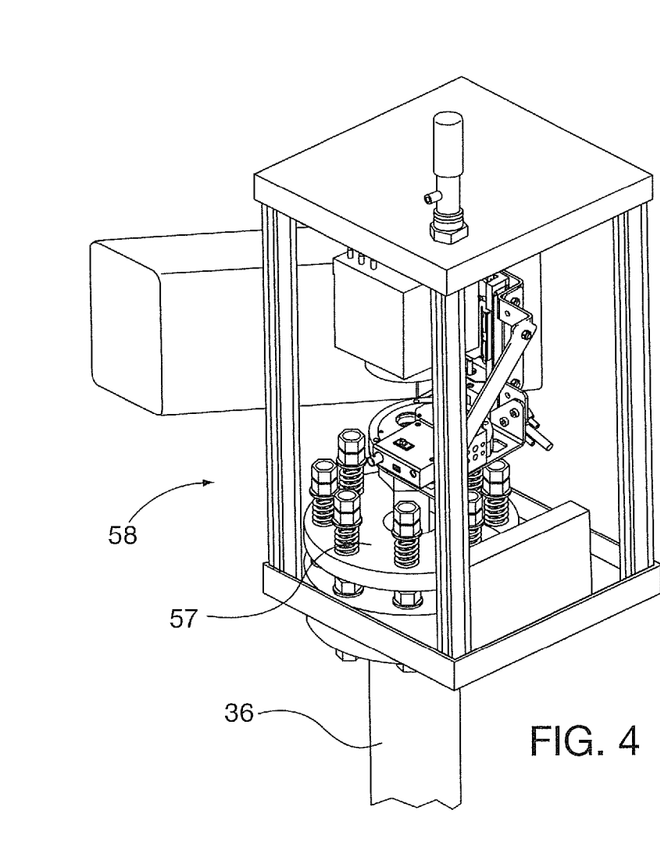
FIG. 4 is a schematic elevational perspective view of an inspection system of the present invention coupled to a gas turbine inspection port.
Figure 5:
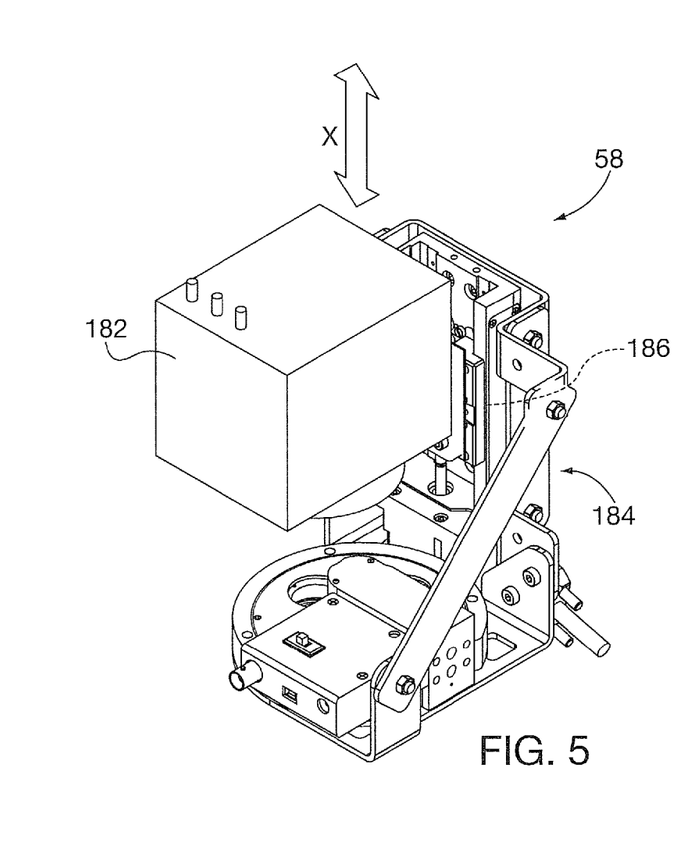
FIG. 5 is schematic elevational perspective view an inspection camera focus adjustment mechanism of an inspection system of the present invention.

The camera enclosure 58 hardware components that are coupled to the optical tube housing 54 are shown in FIGS. 4 and 5. The optical tube 54 and camera imaging system enclosure 58 are coupled to a turbine inspection port 36 by a port flange mounting ring 57 of known construction that seals the inspection port. A known imaging camera 182 mounts on a camera focus drive 184, with a known servo motor/position encoder 186, that is capable of translating the camera along focus X directional arrow.

Figure 6:
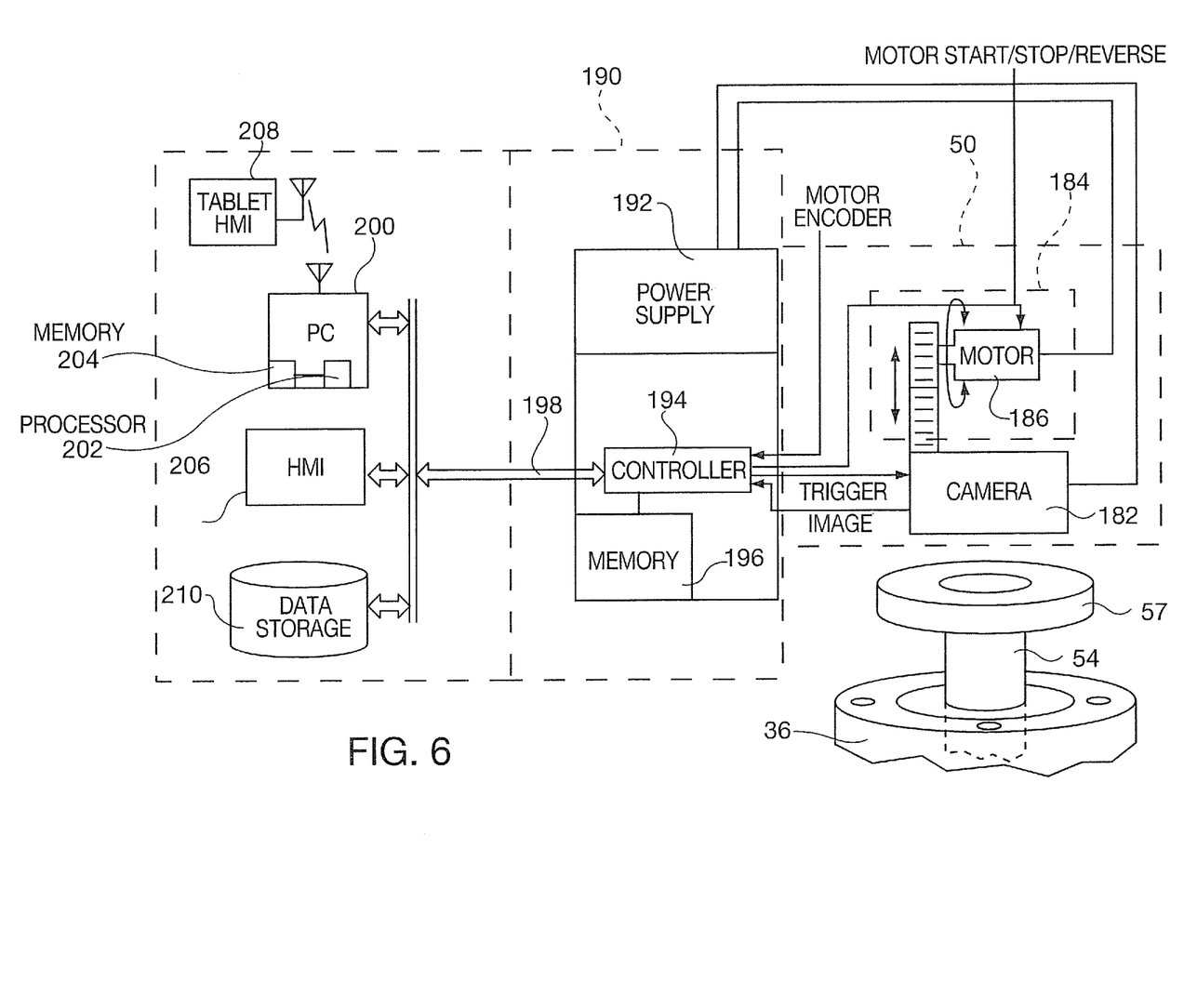
FIG. 6 is a block diagram of an inspection system of the present invention, including the camera inspection system and related electronic/electromechanical control system components.

Referring to FIG. 6, image control system 190 provides power to the camera focus drive motor 186 as well as the camera 182, causes to focus drive motor to start, stop and reverse, based in part on focus drive position information supplied by the encoder of the motor 186, triggers the camera 182 to record images and receives images from the camera for further processing and storage, such as for example performing known non-contact temperature sensing by monitoring and correlation of IR wavelength emissions of an object within the optical tube viewing port 56 field of view. The image control system 190 includes a known controller 194 that executes program instructions stored in memory 196. The controller 194 is in communication via a bidirectional data pathway (e.g., a cable and/or data bus implementing Ethernet communications protocol) with a host controller 200. An exemplary host controller 200 is a personal computer (PC) having a processor 202 implementing programming instructions accessible in memory 204. A known human machine interface (HMI) 206 is in communication with the PC in order to implement human command, control and monitoring. The PC may also communicate with other HMI devices, such as tablet computer 208 via a known wireless communication protocol, such as Bluetooth protocol. The image control system may include a data storage device to store, process and archive images and/or correlated temperature readings received from the camera 182.

Prior to starting a gas turbine that is to be inspected, one or more camera inspection systems 50 are individually coupled to respective desired turbine inspection ports 36, etc., by inserting the optical tube housing 54, therein and affixing the port flange mounting ring 57 to the inspection port. The camera 182 captures images of areas of interest within the gas turbine internal components in response to trigger commands received from the image control system 190 and transfers the captured images to the image control system for subsequent processing (e.g., for turbine blade surface temperature sensing) and archiving.

Using reflective mirror arrays in the camera inspection system optical tubes of the present invention provides at least the following benefits over traditional refractive lens optical tubes:

1. Improved image quality over a broad spectral range: unlike refractive lens optical tubes, reflective mirror array optical tubes are capable of transmitting images over a wide spectral bandwidth of 550 nm to 20 μm with no chromatic aberration and thus provide an advantage when forming a high quality image from the visible to the long IR.

2. Given the wide spectral bandwidth of reflective mirror array optical tubes, a single optical tube design can be used to inspect both metal surface and thermal bond coated surface turbine blades in the near and long IR ranges. In refractive optical tube systems, different tube designs would be needed for each portion of the IR range. Long IR range refractive lens optical tubes have severe compromises between image quality and tube life.

3. Combined higher temperature operability and service life: reflective mirror lens arrays utilized in the present invention optical tubes are capable of continuous operation at temperatures greater than 932 degrees Fahrenheit (500 degrees Celsius), while providing good quality images in a broad spectrum of wavelengths. In contrast, refractive materials capable of transmitting comparable images in the long IR wavelength range (8-12 µm) are not capable of operating for sustained periods at temperatures greater than 500 degrees Celsius. Embodiments of the present invention seal the optical tube with an external refractive pressure window having complimentary transmission quality in the long IR wavelength range. The window is oriented at the distal end of the optical tube external the turbine inspection port. The window's operational temperature does not exceed 300° C., and is capable of continuous operation.

Although various embodiments that incorporate the teachings of the present invention have been shown and described in detail herein, those skilled in the art can readily devise many other varied embodiments that still incorporate these teachings.

What is claimed is:

1. A turbine visual image inspection apparatus comprising:
   an optical tube housing having a viewing port; and
   a visual image reflective mirror array within the optical tube housing in optical alignment with the viewing port, having a concave objective mirror for capturing an optical visual image within its objective field of view and a convex focal mirror for focusing the captured image on a focal plane, the mirrors having spectral reflectivity from 550 nm to 20 µm, and capable of continuous operation at temperatures greater than 932 degrees Fahrenheit (500 degrees Celsius).

2. The apparatus of claim 1, at least one mirror in the mirror array further comprising a metal or glass substrate that is coated with a reflective metal layer.

3. The apparatus of claim 2, further comprising the at least one mirror is coated with a gold (Au) or molybdenum (Mb) reflective layer.

4. The apparatus of claim 1, further comprising a transparent window mounted within the housing distal from the viewing port and in optical alignment with the viewing port and the reflective mirror array, the window having a spectral transmission band from 550 nm to 20 µm and capable of continuous operation at temperatures greater than 572 degrees Fahrenheit (300 degrees Celsius).

5. The apparatus of claim 4, the transparent window comprising zinc selenide (ZnSe).

6. The apparatus of claim 5, further comprising at least one mirror in the mirror array coated with a gold (Au) or molybdenum (Mb) reflective metal layer.

7. The apparatus of claim 1, the mirror array comprising a mirror relay in the optical tube between the objective and focal mirrors, in optical alignment therewith and each other.

8. The apparatus of claim 1, further comprising a gas turbine engine having thermal barrier coated blades, and an inspection port, wherein the optical tube housing viewing port is inserted in the inspection port, for generating images of a turbine blade that is oriented within a field of view established by the inspection apparatus.

9. A turbine engine visual image camera inspection system comprising:
   an optical tube housing having a viewing port;
   at least one visual image reflective mirror array within the optical tube housing in optical alignment with the viewing port, having a concave objective mirror for capturing an optical visual image within its objective field of view and a convex focal mirror for focusing the captured image on a focal plane, the mirrors having spectral reflectivity from 550 nm to 20 µm, and capable of continuous operation at temperatures greater than 932 degrees Fahrenheit (500 degrees Celsius);
   a transparent window mounted within the housing distal from the viewing port and in optical alignment with both the viewing port and the reflective mirror array, the window having a spectral transmission band from 550 nm to 20 µm and capable of continuous operation at temperatures greater than 572 degrees Fahrenheit (300 degrees Celsius);
   the reflective mirror array or a series of optically aligned arrays transmitting within the housing through the window a captured image of an object of interest that is oriented within the objective field of view established by the concave objective mirror; and
   a camera coupled to the housing in optical alignment with the window and the reflective mirror array or arrays, for capturing images transmitted through the reflective array or arrays.

10. The system of claim 9, further comprising at least one mirror of the reflective array or arrays coated with a reflective metal layer.

11. The system of claim 10, further comprising at least one mirror of the reflective array is coated with a gold (Au) or molybdenum (Mb) reflective layer.

12. The system of claim 9, the transparent window comprising zinc selenide (ZnSe).

13. The system of claim 9, the mirror array comprising a mirror relay array in the optical tube between the objective and focal mirrors, in optical alignment therewith and each other.

14. The system of claim 13, further comprising a plurality of mirrors in each of the plurality of reflective mirror arrays are coated with a gold (Au) or molybdenum (Mb) reflective layer.

15. The system of claim 9, further comprising a gas turbine engine having an inspection port, wherein the housing viewing port is inserted in the inspection port before gas turbine operation and the system generates images of areas of interest within the gas turbine during turbine operation.

16. The system of claim 9, further comprising a gas turbine engine having thermal barrier coated blades, and an inspection port, wherein the optical tube housing viewing port is inserted in the inspection port, for generating images of a turbine blade that is oriented within a field of view established by the lens array.

17. A method for visually inspecting areas of interest within an operating gas turbine engine, comprising:
   providing an IR camera visual image inspection system having:
      an optical tube housing having a viewing port;
      at least one visual image reflective mirror array within the optical tube housing in optical alignment with the viewing port, having a concave objective mirror for capturing an optical visual image within its objective field of view and a convex focal mirror for focusing the captured image on a focal plane, the mirrors having spectral reflectivity from 550 nm to 20 µm, and capable of continuous operation at temperatures greater than 932 degrees Fahrenheit (500 degrees Celsius);

a transparent window mounted within the housing distal from the viewing port and in optical alignment with both the viewing port and the reflective mirror array, the window having a spectral transmission band from 550 nm to 20 μm and capable of continuous operation at temperatures greater than 572 degrees Fahrenheit (300 degrees Celsius);

the reflective mirror array or a series of optically aligned arrays transmitting within the housing through the window a captured image of an object of interest that is oriented within the objective field of view established by the concave objective mirror; and a camera coupled to the housing in optical alignment with the window and the reflective mirror array or arrays, for capturing images transmitted through the reflective array or arrays;

inserting the camera inspection system housing viewing port into an inspection port of a gas turbine engine; and generating images of areas of interest within the gas turbine engine during turbine operation.

18. The method of claim 17, further comprising selectively generating images of a turbine blade with high emissivity in a near infra-red (IR) wavelength of approximately 1-2 μm or a thermal barrier coated turbine blade with high emissivity in a long IR wavelength of approximately 8-12 μm, the image generating performed with the same optical tube housing and mirror array therein, for either type of turbine blade.

19. The method of claim 18, further comprising determining temperature of a turbine blade with high emissivity within a near infra-red (IR) wavelength of approximately 1-2 μm or a thermal barrier coated turbine blade with high emissivity within a long IR wavelength of approximately 8-12 μm, the temperature determining performed with the same optical tube housing and mirror array therein, for either type of turbine blade.

20. The method of claim 17, further comprising operating the visual image inspection system continuously during the gas turbine engine operation between scheduled maintenance cycles of up to 4000 hours.

\* \* \* \* \*